United States Patent [19]

Barken

[11] Patent Number: 4,672,963
[45] Date of Patent: Jun. 16, 1987

[54] APPARATUS AND METHOD FOR COMPUTER CONTROLLED LASER SURGERY

[76] Inventor: Israel Barken, 532 North Caribe, Tucson, Ariz. 85716

[21] Appl. No.: 742,278

[22] Filed: Jun. 7, 1985

[51] Int. Cl.$^4$ ............................................. A61B 17/36
[52] U.S. Cl. .................................................. 128/303.1
[58] Field of Search ...................... 128/6, 24 A, 303.1, 128/395–398, 660; 219/121 LU, 121 LV

[56] References Cited

U.S. PATENT DOCUMENTS

| | | | |
|---|---|---|---|
| 3,764,775 | 10/1973 | Hasslinger et al. | 219/121 LU |
| 4,084,582 | 4/1978 | Nigam | 128/660 |
| 4,211,229 | 7/1980 | Wurster | 128/395 |
| 4,341,120 | 7/1982 | Anderson | 128/660 |
| 4,391,282 | 7/1983 | Ando et al. | 128/660 |
| 4,448,201 | 5/1984 | Matsumoto | 128/660 |

FOREIGN PATENT DOCUMENTS

| | | | |
|---|---|---|---|
| 8500510 | 2/1985 | PCT Int'l Appl. | 128/660 |
| 8501445 | 4/1985 | PCT Int'l Appl. | 128/395 |

OTHER PUBLICATIONS

"A Binocular Stereoscopic Display System for Echocardiography", Nakatani et al., IEEE Trans. Bio. Eng., Feb. 1979.
"High-Resolution Echocardiography", NASA, NASA Tech. Brief, 1979.
"A Computer-aided 3-D Display System for U.S. Diagnosis of a Breast Tumor, Itoh et al., Ultrasonics, Nov. 1979.

Primary Examiner—Kyle L. Howell
Assistant Examiner—Max F. Hindenburg
Attorney, Agent, or Firm—David G. Rosenbaum

[57] ABSTRACT

A surgical system for destroying unwanted internal structures including a laser device, an ultrasonic probe and a computer system is described. The ultrasonic probe provides data signals that are processed by the computer system to provide an image of the structures involved in the laser irradiation procedure. The laser device can be inserted in the body and activated by the computer system to provide radiation capable of destroying internal tissue. By calibrating the effects of the laser device as a function of power, the surgical procedure can be controlled by including overlaying images of the regions already affected by the surgical procedures on the images previously provided by the ultrasonic probe. This image reconstruction can be performed in real time providing immediate feedback to the attending physician. The computer system can also monitor system parameters such as laser power. This system has particular application to procedures involving the prostate gland where the laser light guide can be inserted intraurethrally and the ultrasonic probe can be inserted intraurethrally or transrectally.

10 Claims, 3 Drawing Figures

APPARATUS AND METHOD FOR COMPUTER CONTROLLED LASER SURGERY

BACKGROUND OF THE INVENTION

1. Field of the Invention

This invention relates generally to laser surgery and, more particularly, to an automated and integrated system including a laser device, an ultrasonic probe and a computer system for use in performing internal surgery. The computer system provides a display of tissue within the patient. The attending physician provides input into the computer with a light pen describing tissue to be irradiated. The computer system then controls both the duration and intensity of the laser burst to accomplish tissue destruction.

2. Description of the Related Art

The use of laser radiation to destroy certain types of structures and/or selected tissues has become increasingly prevalent in recent years. The laser radiation has the advantage that the intense heat generated by the laser can be focused quite precisely and can therefore be used for controlled destruction of a predetermined region of the body with minimal damage to the surrounding and/or connecting tissue. The use of laser radiation in surgical procedures can have the benefit that open-surgery on the patient can frequently be eliminated and the associated trauma avoided. The tissue destroyed by laser radiation can typically by removed from the interior of the body by normal bodily processes.

For example, in the urologic surgery, in which open surgery is not performed, electrocautery resection has been typically employed. However, advantages of the use of laser radiation replacing this type of surgical procedure has been documented, c.f. "Laser Photoradiation in Urologic Surgery," by Joseph A. Smith, Jr. and John A. Dickson; the Journal of Urology; Vol. 31, April 1984, p. 631-635.

In using laser techniques in non-open surgery, the laser radiation, applied to the selected structure via a light pipe, can be guided either by a predetermined positioning apparatus such as is described in U.S. Pat. No. 4,469,098 entitled, "Apparatus for and Method of Utilizing Energy to Excise Pathological Tissue," or can be guided by a cystoscope or light pipe in which the areas to be eradiated by the radiation can be identified by visual inspection such as are described in U.S. Pat. No. 4,454,882 entitled, "Laser Apparatus for Utilizing Marking Laser for Triggering Operative Laser." While this technique is generally satisfactory for tumors located on the surface of internal tissues or structures and for resectioning small structures themselves, the removal of a larger internal structure, such as an entire prostate gland, the positioning of the laser light guide with respect to the selected structure becomes crucial to the success of the procedure.

A need has therefore been felt for apparatus and method for utilizing laser radiation in non-open surgical procedures that would permit precise definition of the region of tissue to be destroyed and can, in addition, provide region definition in real time.

SUMMARY OF THE INVENTION

It is therefore an object of the present invention to provide an improved technique for precise and controlled destruction of internal bodily structures.

It is a further object of the present invention to provide an improved technique for using laser radiation to precisely locate and destroy unwanted internal tissues in the body.

It is a more particular object of the present invention to use ultrasonic imaging techniques to control the position of a light guide transmitting laser radiation to a predetermined structure during a tissue destruction procedures.

It is another more particular object of the present invention to provide apparatus and method for destroying a portion or all of a prostate gland without utilizing the techniques of open surgery to obtain access to the structure.

The aforementioned and other objects are accomplished, according to the present invention, by monitoring the position of the laser light guide transmitting the laser radiation to selected internal structures and performing a controlled irradiation of internal structures through the use of an ultrasonic probe. The ultrasonic probe is coupled to a computer system for providing a multiplicity cross-section images of the internal body structure. By varying the position of the ultrasonic probe along a known longitudinal dimension, a three-dimensional image of a structure can be reconstructed from the two-dimensional images. The images can be interpreted by a computer system or by the computer system in conjunction with the physician and can be used to control the parameters of a surgery, such as energy requirements for irradiated tissue during the performance of a laser radiation procedure and/or can be used in real time to locate the present position of the light pipe carrying the laser radiation. As an example, for the removal of the prostate gland, the ultrasonic probe can be entered in the patient transrectally and the laser probe can be entered in the patient intraurethrally. The position and therefore the destructive region of the laser radiation can be determined by the images produced by the ultrasonic probe and computer system or by knowing the range of radiation damage in conjunction with the position and power of laser device activation.

These and other features of the present invention can be understood upon reading of the following description along with the Figures.

DETAILED DESCRIPTION OF THE FIGURES

Figure 1:
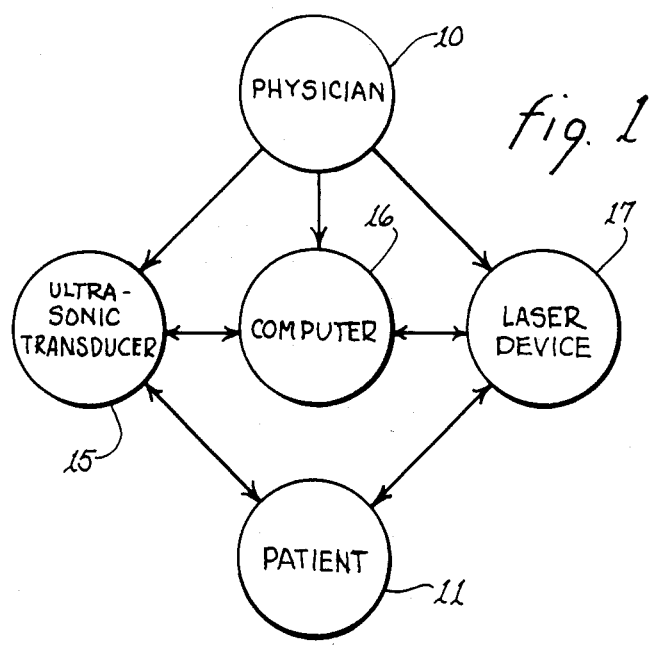
FIG. 1 is a general diagram illustrating the system for performing the surgical technique of the instant invention.

Referring to FIG. 1, a general diagram of the computerized ultrasound laser surgery (CULS) system is shown. The physician 10 has at his disposal and under his control an ultrasonic transceiver device 15, a laser device 17 and a computer system 16. The ultrasonic transceiver device and the laser device interact directly with the patient 11. The computer system 16 processes information from the ultrasonic transceiver device 15 to provide an image on an associated monitor. In addition, the computer system 16 monitors and controls the activity (i.e. activation and power) of the laser device 17. The physician, based on the images provided by the computer system, can control the position of the ultrasonic transceiver device and can control positioning and activation of the laser device. The physician can enter data into the computer system through an interactive display. It will be clear that for other purposes such as monitoring bodily parameters, administering anesthesia, etc., the attending physician and/or associated medical personnel can additionally interact with the patient.

Figure 2:
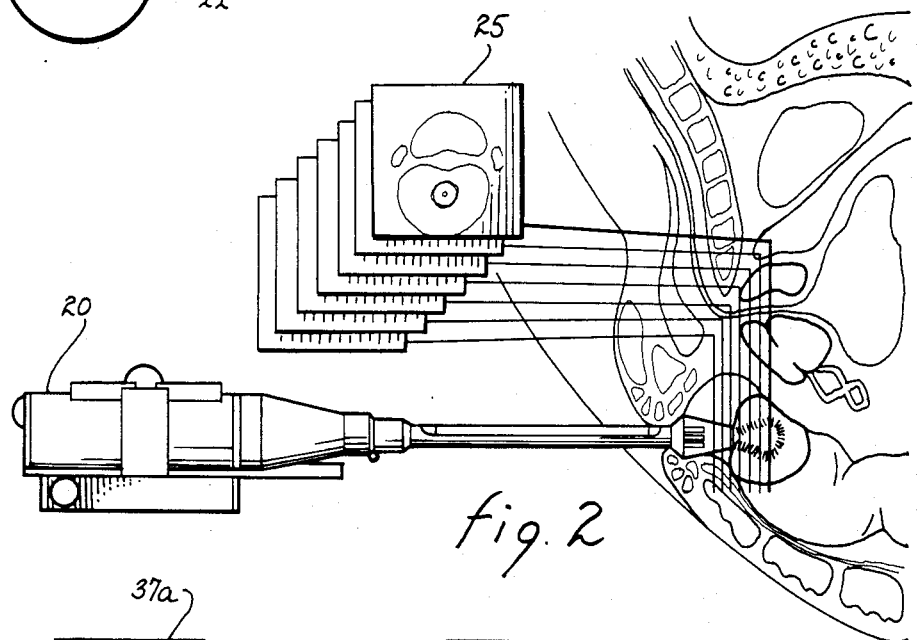
FIG. 2 is a schematic illustration of how the ultrasonic probe can provide a three-dimensional image of an internal organ (i.e. the prostate gland) utilizing a plurality of planal images.

Referring to FIG. 2, a schematic diagram of the reconstruction of an internal structure is shown. The ultrasonic transceiver 20 is inserted into the patient 11 through a body opening (e.g. transrectally). Once inserted in the opening, a series of cross-sectional images 25 can be provided that define the selected structure (e.g. the prostate gland 28) under investigation by knowing the relative location 26 of the ultrasonic transducer probe in the body. Therefore, a three-dimensional image can be reconstructed of the structure under investigation by an accumulation of planar images of known separation.

Figure 3:
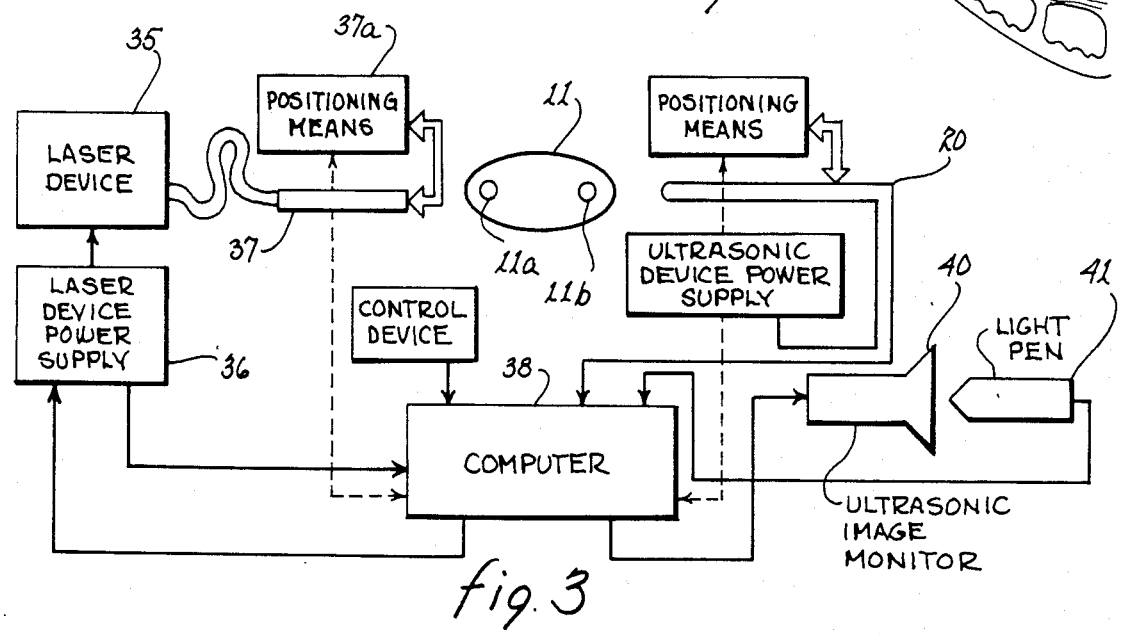
FIG. 3 is a schematic diagram of the use of an ultrasonic probe and a laser device during a surgical procedure according to the instant invention.

Referring next to FIG. 3, a diagram of the present invention is shown. A power supply 36 controls the output of a laser unit 35. The laser radiation is entered into a laser fiberoptic conduit or light guide 37 and the laser light guide is inserted into a body opening (e.g. the urethral canal 11a) of patient 11. The laser light guide 37 is typically under the control either directly or indirectly of the attending physician. An ultrasonic device power supply 39 applies electrical signals into the ultrasonic transceiver 20 which is inserted into a second body opening (e.g. the rectal canal 11b) of the patient 11. The reflected waves from the ultrasonic probe are detected by the ultrasonic transceiver after being processed by the computer system and are transmitted to the ultrasonic monitor 40. The monitor can provide a real time cross-sectional image determined by the position of the transceiver. The motion of the ultrasonic transceiver relative to patient 11 at the same time provides a facility for monitoring of the image on the ultrasonic monitor 40 through a light pen 41. The ultrasonic transceiver 20 is positioned by position means 20a and the laser light pipe is positioned by positioning means 37a. The position means can be members of the medical staff and/or devices controlled by signals from the computer system 36. The ultrasonic power supply, the laser power supply and the light pen are controlled by a computer system 36 which, in turn, can be under the control of a control circuit 32. The computer system is used to automate the surgical procedure to the maximum extent possible, while still maintaining the control of the procedure by the attending physician.

OPERATION OF THE PREFERRED EMBODIMENT

Although the present invention has applicability to any non-open surgical procedure, the immediate anticipated use is laser irradiation causing destruction of the prostate gland. Normal bodily functions will cause the dead tissue to slough out of the body. The prostrate gland provides clearly definable ultrasonic image signature when viewed on a monitor for using ultrasonic techniques. The prostate gland is important because benign prostratic hypertrophy affects every man above the age 50 with clinical representation at the age of 60. In addition, cancer of the prostate gland is the second largest killer of the U.S. male population. Furthermore, the prostrate gland is relatively accessible through the urethral canal. The surgical procedures involved removal by radical surgery the prostate gland can have severe adverse side effects. The relatively non-traumatic surgical technique of the instant invention, for partial or complete destruction with subsequent sloughing of the prostate gland, minimizes the side effects and can be performed with local anesthetic techniques. The destroyed tissue will not normally be removed during performance of these procedures but typically will be removed by normal body functions.

The operation of the present invention envisions that the images of the ultrasonic probe can be used in conjunction with the computer system to provide an image of the entire structure (in this case the prostate gland). The images of the ultrasonic probe serve the additional function that the position of the laser light guide can also be monitored in real time. The light pen and the video monitor, in conjunction with the computer system, form the basis to control the activation and the strength of the laser irradiation means within the patient. The light pen is under the control of the attending physician at all times. The attending physician would provide an input into the computer system via the light pen and video monitor combination. This input would in turn cause laser irradiation to take place within the patient. Depending on the energy of the laser radiation, the depth of penetration through tissue regions can vary. This depth of penetration of the destructive radiation can be determined experimentally so that the procedure can involve the predetermined region. The computer system can determine the location and size of the tumors using data from the ultrasonic probe and based on this information, the computer system can determine the total power intensity, pulse duration and repetition rate of the laser that is required for accurate and complete removal of the unwanted tissue. In addition, the computer system can be programmed to provide real time color graphic information of structures having distinct ultrasonic signatures, such as the capsule wall or a tumor module. If the effect of laser radiation as a function of power density is known, the computer system can include in the image the information with respect to the tissue already destroyed by the laser radiation. This information can be entered into the computer system in a variety of ways. If the irradiated tissue provided a distinct image signature under inspection by the ultrasonic probe, then this signature can be imaged on the monitor automatically with a separate color. If a distinct signature is not provided by the ultrasonic probe, then the use of the interactive display can permit the information to be entered manually provided, of course, the position of the laser light guide is known at the moment of laser device activation. This position can be determined by the ultrasonic probe or can be determined by appropriate calibrated positioning apparatus. In either procedure, the display can be provided in real time. Indeed, the computer system can be used to disable the laser device when the position of the light guide is determined to be capable of irradiation of healthy tissues. To the extend that the position of the laser light guide can be automatically determined relative to the unwanted tissue, and to the extent an irradiated (i.e. destroying) tissue regions can be determined automatically, the procedure can then be automated.

It will be clear that the light guide of the laser radiation can be associated with apparatus such as a cystoscope for visual inspection during the procedure. This apparatus can provide an additional source of information and control.

The above description is included to illustrate the operation of the preferred embodiment and is not meant to limit the scope of the invention. The scope of the invention is to be limited only by the following claims. Many variations will be apparent to one skilled in the art that can yet be encompassed by the spirit and scope of the invention.

It will be further clear to those skilled in the art that the ultrasonic probe, for some applications, does not need to be inserted within the body but can have the position varied in a known manner over an external area for investigation of certain bodily structures. And the relatively thin optical light guide can be inserted into the body with a relatively small surgically created opening in the exterior of the body, creating relatively minor trauma to the patient.

What is claimed is:

1. Apparatus for destroying unwanted internal tissue comprising:
    ultrasonic probing means for applying ultrasonic signals to an internal body region of a patient;
    laser irradiation means for irradiating pre-determined areas of said internal body region of said patient;
    ultrasonic receiving means for receiving said applied ultrasonic signals, said applied ultrasonic signals conveying information about tissue in said internal body region and information about the position of said laser irradiation means in said internal body region of the patient; and
    computer means for receiving said conveyed tissue and laser irradiation means information, said computer means controlling both intensity and duration of energy emitted by said laser irradiating means based upon said conveyed information.

2. Apparatus for destroying unwanted internal tissue as claimed in claim 1 wherein said ultrasonic probing means and said ultrasonic receiving means are both located externally to the body of said patient.

3. Apparatus for destroying unwanted internal tissue as claimed in claim 1 further comprising:
    display means for receiving a representation of an image of said internal body region generated by said computer means.

4. Apparatus for destroying unwanted internal tissue as claimed in claim 3 further comprising:
    input means connected to said display means and said computer means for receiving input from an operator to delimit healthy internal tissues from unwanted internal tissues, wherein said computer means controlling both said intensity and said duration of said energy emitted by said laser irradiating means can modify said intensity and said duration because of said delimiting.

5. Apparatus for destroying unwanted internal tissue as claimed in claim 4 wherein said computer means further comprises disabling means for disabling said laser irradiating means when the position of said laser irradiating means is such as to irradiate health tissue.

6. Apparatus for destroying unwanted internal tissue as claimed in claim 5 wherein said ultrasonic probing means and said ultrasonic receiving means are both located internally to the body of said patient.

7. Apparatus for destroying unwanted internal tissue as claimed in claim 6 wherein
    said unwanted tissue is a prostate gland;
    said ultrasonic probing means and said ultrasonic receiving means are a single unit and designed to be inserted transrectally; and
    said laser irradiating means is designed to be inserted intraurethrally.

8. A method for destroying unwanted internal tissue comprising the steps of:
    inserting laser irradiation means through a bodily opening of a patient;
    ultrasonically probing to determine the position of said laser irradiating means and the unwanted internal tissue within said bodily opening;
    providing ultrasonic output from said probing step to computer means for controlling the energy output of said laser irradiating means and accepting input from an operator wherein said computer means further comprises a real time ultrasonic display of the internal tissue of the patient and delimiting input means for delimiting, on said ultrasonic display, the tissue area to be irradiated, said delimiting input means being electronically coupled to said ultrasonic display and said computer means;
    delimiting, by said delimiting input means, the tissue area to be irradiated by said laser irradiating means;
    positioning said laser irradiating means such that laser energy emanating from said laser irradiating means will destroy only unwanted internal tissue delimited by said delimiting input means;
    computing optimum power and duration of energy to be applied to said laser irradiating means, said step of computing being done by said computer means;
    controlling the power and duration of the energy applied to said laser irradiating means with said computer means; and
    irradiating said unwanted internal tissue with said laser energy.

9. The method of destroying unwanted internal tissue of claim 8 further comprising the steps of:
    determining with said computer means if said power and duration of said energy applied to said laser irradiating means will harm healthy tissue;
    disabling said power and duration of said energy applied to said laser irradiating means if said step of determining yields a possibility of harm to healthy tissue.

10. A method for destroying an unhealthy prostate gland compris the steps of:
    inserting a laser irradiating means intraurethrally into a patient;
    inserting an ultrasonic probe means transrectally into said patient;
    probing to determine the position of said laser irradiating means relative to the prostate gland within said patient.
    providing output from said probing step to a computer means;
    providing a display of said prostate gland, tissue surrounding said prostate gland, and said laser irradiating means within said patient;
    accepting input delimiting healthy internal tissue from said prostate gland;
    positioning said laser irradiating means such that laser energy emanating from said laser irradiating means will destroy said prostate gland;
    computing optimum power and duration of energy to be applied to said laser irradiating means, said step of computing being done by said computer means;

controlling said power and duration of said energy applied to said laser irradiating means with said computer means;

determining with said computer means if said power and duration of said energy applied to said laser irradiating means will harm healthy tissue;

disabling said power and duration of said energy applied to said laser irradiating means if said step of determining yields a possibility of harm to healthy tissue;

radiating said prostate gland tissue with said laser energy; and thereafter providing a display of said prostate gland, said display showing results of said step of radiating.

* * * * *